United States Patent
Rothrock et al.

(10) Patent No.: US 11,721,115 B2
(45) Date of Patent: Aug. 8, 2023

(54) SYSTEMS AND METHODS FOR PROCESSING IMAGES TO DETERMINE IMAGE-BASED COMPUTATIONAL BIOMARKERS FROM LIQUID SPECIMENS

(71) Applicant: PAIGE.AI, Inc., New York, NY (US)

(72) Inventors: Brandon Rothrock, New York, NY (US); Jillian Sue, New York, NY (US); Matthew Houliston, Boston, MA (US); Patricia Raciti, New York, NY (US); Leo Grady, Darien, CT (US)

(73) Assignee: Paige.AI, Inc., New York, NY (US)

( * ) Notice: Subject to any disclaimer, the term of this patent is extended or adjusted under 35 U.S.C. 154(b) by 0 days.

(21) Appl. No.: 17/519,847

(22) Filed: Nov. 5, 2021

(65) Prior Publication Data

US 2022/0138450 A1    May 5, 2022

Related U.S. Application Data

(63) Continuation of application No. 17/511,871, filed on Oct. 27, 2021.
(Continued)

(51) Int. Cl.
*G06V 20/69* (2022.01)
*G06T 7/11* (2017.01)
(Continued)

(52) U.S. Cl.
CPC ........ *G06V 20/695* (2022.01); *G06F 18/2431* (2023.01); *G06N 20/00* (2019.01);
(Continued)

(58) Field of Classification Search
CPC . G06T 2207/20081; G06T 7/11; G06K 9/628; G06N 20/00; G06V 20/695
See application file for complete search history.

(56) References Cited

U.S. PATENT DOCUMENTS 10,113,966 B2 * 10/2018 Yamada ................. G01N 33/80
10,937,541 B2 * 3/2021 Ceballos Lentini .. G06T 7/0012
(Continued)

OTHER PUBLICATIONS

Jimenez-Carretero, D. "Tox_(R)CNN: Deep learning-based nuclei profiling tool for drug toxicity screening" PLOS Computational Biology (Nov. 30, 2018)—pp. 1-23.*
(Continued)

*Primary Examiner* — Mia M Thomas
(74) *Attorney, Agent, or Firm* — Bookoff McAndrews, PLLC (57) ABSTRACT

A method of using a machine learning model to output a task-specific prediction may include receiving a digitized cytology image of a cytology sample and applying a machine learning model to isolate cells of the digitized cytology image. The machine learning model may include identifying a plurality of sub-portions of the digitized cytology image, identifying, for each sub-portion of the plurality of sub-portions, either background or cell, and determining cell sub-images of the digitized cytology image. Each cell sub-image may comprise a cell of the digitized cytology image, based on the identifying either background or cell. The method may further comprise determining a plurality of features based on the cell sub-images, each of the cell sub-images being associated with at least one of the plurality of features, determining an aggregated feature based on the plurality of features, and training a machine learning model to predict a target task based on the aggregated feature.

15 Claims, 6 Drawing Sheets

Related U.S. Application Data (60) Provisional application No. 63/107,389, filed on Oct. 29, 2020.

(51) Int. Cl.
  *G06K 9/62* (2022.01)
  *G06N 20/00* (2019.01)
  *G06T 7/194* (2017.01)
  *G16H 30/40* (2018.01)
  *G06T 7/00* (2017.01)
  *G06F 18/2431* (2023.01)

(52) U.S. Cl.
  CPC .............. *G06T 7/0012* (2013.01); *G06T 7/11* (2017.01); *G06T 7/194* (2017.01); *G06V 20/698* (2022.01); *G16H 30/40* (2018.01); *G06T 2207/20081* (2013.01); *G06T 2207/30024* (2013.01)

(56) References Cited

U.S. PATENT DOCUMENTS

| | | | | |
|---|---|---|---|---|
| 11,176,676 | B2* | 11/2021 | Rothrock | G06T 7/194 |
| 2010/0054574 | A1* | 3/2010 | Marcelpoil | G01N 15/1475 |
| | | | | 382/133 |
| 2010/0254589 | A1* | 10/2010 | Gallagher | G06V 20/695 |
| | | | | 382/133 |
| 2012/0237109 | A1* | 9/2012 | Rajpoot | G06T 7/0012 |
| | | | | 382/128 |
| 2016/0239962 | A1* | 8/2016 | Markin | G06T 7/0014 |
| 2017/0161545 | A1* | 6/2017 | Champlin | G06V 20/695 |
| 2017/0169567 | A1* | 6/2017 | Chefd'Hotel | G06T 7/0012 |
| 2017/0356976 | A1* | 12/2017 | Shapiro | G06V 10/82 |
| 2017/0372117 | A1* | 12/2017 | Bredno | G06T 7/00 |
| 2019/0147215 | A1* | 5/2019 | Al-Kofahi | G06T 7/143 |
| | | | | 382/133 |
| 2019/0206055 | A1* | 7/2019 | Gurcan | G06T 7/11 |
| 2019/0251687 | A1* | 8/2019 | Madabhushi | G06K 9/6223 |
| 2019/0259154 | A1* | 8/2019 | Madabhushi | G06T 7/0012 |
| 2020/0160032 | A1 | 5/2020 | Allen et al. | |
| 2020/0184641 | A1* | 6/2020 | Schmidt | G06T 7/35 |
| 2020/0381104 | A1* | 12/2020 | Ceballos Lentini | G16H 50/20 |
| 2020/0394794 | A1* | 12/2020 | Park | G01B 9/021 |
| 2021/0073986 | A1* | 3/2021 | Kapur | G06T 7/0012 |
| 2021/0334972 | A1* | 10/2021 | NarasimhaMurthy | |
| | | | | G01N 35/00732 |
| 2022/0130049 | A1* | 4/2022 | Song | G06T 7/162 |
| 2022/0366710 | A1* | 11/2022 | Gildenblat | G06V 10/809 |

OTHER PUBLICATIONS

Putzu Lorenzo et al: "Leucocyte classification for leukaemia detection using image processing techniques," Artificial Intelligence in Medicine, vol. 62, No. 3, Nov. 1, 2014 (Nov. 1, 2014), pp. 179-191, XP055778740, NL ISSN: 0933-3657, DOI: 10.1016/j.artmed.2014.09.002.

Yang Linfeng et al: "NuSeT: A deep learning tool for reliably separating and analyzing crowded cells," PLOS Computational Biology, vol. 16, No. 9, Sep. 14, 2020 (Sep. 14, 2020), pp. 1-20, XP055887573, DOI: 10.1371/journal.pcbi.1008193.

* cited by examiner

SYSTEMS AND METHODS FOR PROCESSING IMAGES TO DETERMINE IMAGE-BASED COMPUTATIONAL BIOMARKERS FROM LIQUID SPECIMENS

RELATED APPLICATION(S)

This application is a continuation of U.S. application Ser. No. 17/511,871, filed Oct. 27, 2021, which claims priority to U.S. Provisional Application No. 63/107,389 filed Oct. 29, 2020, the entire disclosures of which are hereby incorporated herein by reference in their entireties.

FIELD OF THE DISCLOSURE

Various embodiments of the present disclosure pertain generally to image processing methods. More specifically, particular embodiments of the present disclosure relate to systems and methods for processing electronic images and rapid evaluation of adequacy in specimen preparations.

BACKGROUND

In the field of cancer and other disease diagnosis, diagnostic and screening tests are used to detect disease. Typically, diagnostic tests are conducted if a screening test result is positive. Cytotechnicians are laboratory professionals who review slides of human cells to determine if they are abnormal or diseased. Their initial findings are used by pathologists to render a diagnosis for the disease. Based on the diagnosis, pathologists and physicians can request additional molecular testing (e.g. flow, IHC, FISH, PCR/NGS) to better segment the best treatment pathway for the patient. However, manual or human review of slides can involve disadvantages based on speed, cost, and accuracy.

Cytology tests are a mainstay of malignancy screening because they are easier to acquire, less invasive, less expensive, and result in less complications, compared to manual or human review of tissue slides. They can also be prepared more quickly for pathology diagnosis when compared to tissue samples. They are, however, challenging to diagnose for a myriad of reasons, including: 1) ancillary tests such as immunohistochemistry might not be available, and 2) samples are often scant making a specific diagnosis more difficult. As such, cytology samples are often classified as 'adequate to make a diagnosis' or 'inadequate to make a diagnosis' and then, if adequate, simply categorized (rather than specifically diagnosed) as benign, atypical, suspicious for malignancy, or positive for malignancy. Depending on the results of cytology, a confirmatory tissue sample can be performed, or definitive treatment can be undertaken. In addition to diagnostic information, information about the molecular makeup of the tumor can be obtained from both cytology and tissue samples, providing important guidance on possible non-surgical treatment options. This genetic information however, necessitates enough tumor tissue to be able to test.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for using a machine learning model to output a task-specific prediction.

A method of using a machine learning model to output a task-specific prediction may include receiving a digitized cytology image of a cytology sample and applying a machine learning model to isolate cells of the digitized cytology image. The machine learning model may include identifying a plurality of sub-portions of the digitized cytology image, identifying, for each sub-portion of the plurality of sub-portions, either background or cell, and determining cell sub-images of the digitized cytology image. Each cell sub-image may comprise a cell of the digitized cytology image, based on the identifying either background or cell. The method of using the machine learning model may further comprise determining a plurality of features based on the cell sub-images, each of the cell sub-images being associated with at least one of the plurality of features, determining an aggregated feature based on the plurality of features, and training a machine learning model to predict a target task based on the aggregated feature.

Identifying either background or cell may comprise using a segmentation system and/or a detection system. Using the segmentation system may comprise identifying one or more individual pixels in the digitized cytology image as belonging to a cell or background, classifying one or more cell regions, of a cell of interest, containing the one or more individual pixels into at least one granular structure, and outputting the cell sub-images tightly bounded around the cell of interest within the digitized cytology image.

Identifying either background or cell may comprise using a detection system to identify bounding regions for each of the cell sub-images.

The method may further comprise using the aggregated feature to train a machine learning classifier to predict necessary quantifications for a target task on a per-cell level. Determining the aggregated feature may comprise computing statistics of per-cell classifications, estimating feature means or cluster centers, and/or training deep learning aggregators that combine per-cell features through convolutional or recurrent mechanisms.

The target task may comprise ensuring the cytology sample contains enough material for a user to categorize the cytology sample. The target task may comprise classifying a specimen category from the aggregated feature. The target task may comprise predicting a probability of detecting a specific mutation within a cytology specimen.

A system for using a machine learning model to output a task-specific prediction may comprise at least one memory storing instructions and at least one processor configured to execute the instructions to perform operations. The operations performed by the processor may comprise receiving a digitized cytology image of a cytology sample and applying a machine learning model to isolate cells of the digitized cytology image. Applying the machine learning model may comprise identifying a plurality of sub-portions of the digitized cytology image, identifying, for each sub-portion of the plurality of sub-portions, either background or cell, and determining cell sub-images of the digitized cytology image. Each cell sub-image may comprise a cell of the digitized cytology image, based on the identifying either background or cell. The operations performed by the processor may further comprise determining a plurality of features based on the cell sub-images, each of the cell sub-images being associated with at least one of the plurality of features, determining an aggregated feature based on the plurality of features, and training a machine learning model to predict a target task based on the aggregated feature.

Identifying either background or cell my comprise using a segmentation system and/or a detection system. Using the segmentation system may comprise identifying one or more individual pixels in the digitized cytology image as belonging to a cell or background, classifying one or more cell regions, of a cell of interest, containing the one or more individual pixels into at least one granular structure, and outputting the cell sub-images tightly bounded around the cell of interest within the digitized cytology image.

Identifying either background or cell may comprise using a detection system to identify bounding regions for each of the cell sub-images.

The operations may further comprise using the aggregated feature to train a machine learning classifier to predict necessary quantifications for a target task on a per-cell level. Determining the aggregated feature may comprise computing statistics of per-cell classifications, estimating feature means or cluster centers, and/or training deep learning aggregators that combine per-cell features through convolutional or recurrent mechanisms.

The target task may comprise ensuring the cytology sample contains enough material for a user to categorize the cytology sample. The target task may comprise classifying a specimen category from the aggregated feature. The target task may comprise predicting a probability of detecting a specific mutation within a cytology specimen.

A non-transitory computer-readable medium may store instructions that, when executed by a processor, perform a method of using a machine learning model to output a task-specific prediction. The method may comprise receiving a digitized cytology image of a cytology sample and applying a machine learning model to isolate cells of the digitized cytology image. Applying the machine learning model may include identifying a plurality of sub-portions of the digitized cytology image, identifying, for each sub-portion of the plurality of sub-portions, either background or cell, and determining cell sub-images of the digitized cytology image. Each cell sub-image may comprise a cell of the digitized cytology image, based on the identifying either background or cell. The method of using the machine learning model may include determining a plurality of features based on the cell sub-images, each of the cell sub-images being associated with at least one of the plurality of features, determining an aggregated feature based on the plurality of features, and training a machine learning model to predict a target task based on the aggregated feature. Identifying either background or cell may comprise using a segmentation system and/or a detection system.

It is to be understood that both the foregoing general description and the following detailed description are exemplary and explanatory only, and are not restrictive of the disclosed embodiments.

BRIEF DESCRIPTION OF THE DRAWINGS

The accompanying drawings, which are incorporated in, and constitute a part of, this specification, illustrate various exemplary embodiments and together with the description, serve to explain the principles of the disclosed embodiments.

DESCRIPTION OF THE EMBODIMENTS

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

In the spirit of less invasive screening tests, cytology suffers from limited tumor quantity and an inability to use common ancillary testing for diagnosis refinement, both of which result in less specific diagnostic categorization. Furthermore, as molecular evaluation of the tumor becomes mainstay, the limited sampling performed in cytology may hinder a comprehensive molecular study of the tumor.

Current industry practice includes a patient undergoing cytologic sampling as part of a screening test or limited, less invasive sampling of a suspected malignancy. The pathologist receives the cytologic smears and preparations, and renders a categorical diagnosis of benign, atypical, suspicious for malignancy, or positive for malignancy, after assessing the specimen for adequacy. Occasionally ancillary testing can be performed which consumes previous tumor tissue, which may otherwise be available for optional additional molecular studies.

The nature of tumor preparation in cytology limits a specific diagnosis; limited material can hinder diagnosis and ability to perform ancillary studies as well as time to diagnose specimen and cost.

The systems and methods of this disclosure leverage artificial intelligence (AI) technology to detect cellular features that are necessary for pathological diagnosis, prognostic and treatment decisions. Data and predictions are aggregated and made available instantaneously via any user interface (e.g. through a digital pathology viewing system, report, or laboratory information system, etc.). Machine learning algorithms can rapidly and simultaneously assess for adequacy, categorize the sample into diagnostic categories, and screen for the most likely molecular changes, limiting the total molecular testing performed on a tumor and therefore, increasing the likelihood of a valid molecular result due to sufficient quantities of tumor Thus, the embodiments of this disclosure may allow for rapid evaluation of 'adequacy' in liquid-based tumor preparations; facilitate the diagnosis of liquid based tumor preparations (cytology, hematology/hematopathology); and predict molecular findings most likely to be found in various tumors detected by liquid-based preparations This may enable more accurate diagnosis of tumors on liquid-based preparations, and it may enable physicians to identify patients that may benefit from molecular testing and/or a corresponding treatment sooner.

Figure 1A:
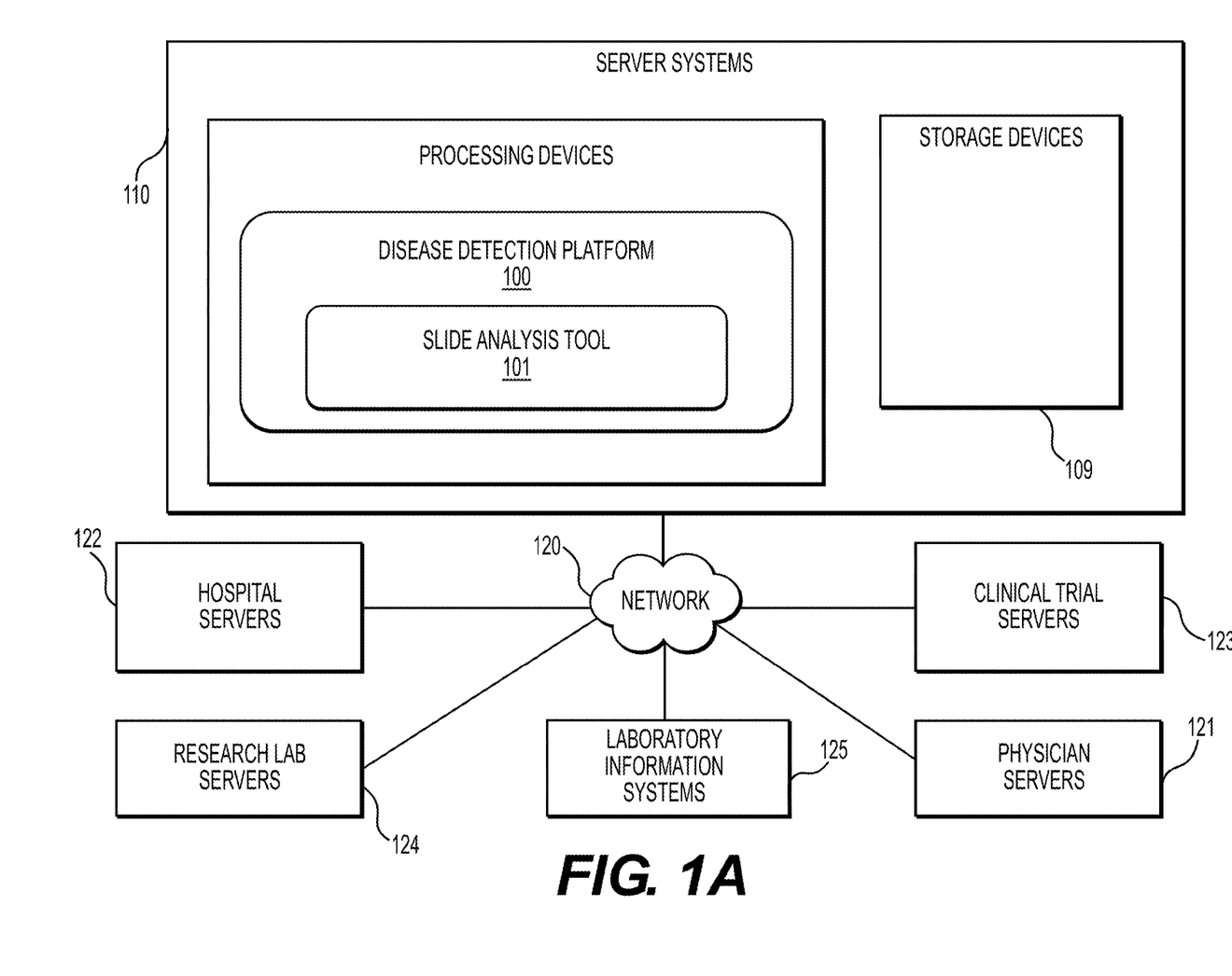
FIG. 1A illustrates an exemplary block diagram of a system and network to detect cellular features from a cytology specimen, according to an exemplary embodiment of the present disclosure.

FIG. 1A illustrates an exemplary block diagram of a system and network to detect cellular features from a cytology sample, according to an exemplary embodiment of the present disclosure.

Specifically, FIG. 1A illustrates an electronic network 120 that may be connected to servers at hospitals, laboratories, and/or doctor's offices, etc. For example, physician servers 121, hospital servers 122, clinical trial servers 123, research lab servers 124, and/or laboratory information systems 125, etc., may each be connected to an electronic network 120, such as the Internet, through one or more computers, servers and/or handheld mobile devices. According to an exemplary embodiment of the present application, the electronic network 120 may also be connected to server systems 110, which may include processing devices that are configured to implement a disease detection platform 100, which includes a slide analysis tool 101 for determining specimen property or image property information pertaining to digital pathology image(s), and using machine learning to determine whether a disease or infectious agent is present, according to an exemplary embodiment of the present disclosure. The slide analysis tool 101 may allow for rapid evaluation of 'adequacy' in liquid-based tumor preparations; facilitate the diagnosis of liquid based tumor preparations (cytology, hematology/hematopathology); and predict molecular findings most likely to be found in various tumors detected by liquid-based preparations.

The physician servers 121, hospital servers 122, clinical trial servers 123, research lab servers 124 and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124 and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124 and/or laboratory information systems 125 may transmit digitized slide images and/or patient-specific information to server systems 110 over the electronic network 120. Server system(s) 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the storage devices 109. Server systems 110 may further include one or more machine learning tool(s) or capabilities. For example, the processing devices may include a machine learning tool for a disease detection platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124 and/or laboratory information systems 125 refer to systems used by pathologists for reviewing the images of the slides. In hospital settings, tissue type information may be stored in a laboratory information system 125.

Figure 1B:
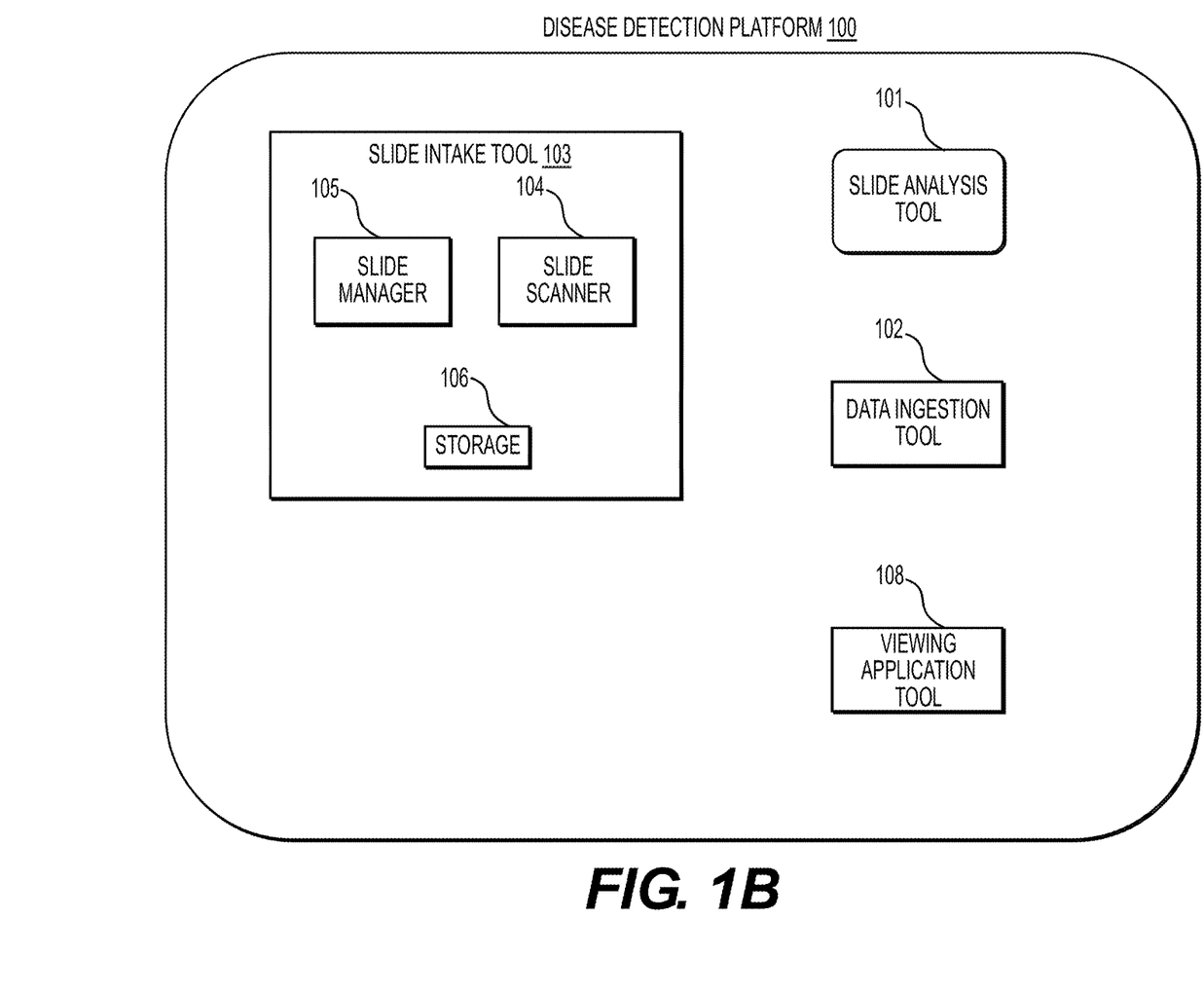
FIG. 1B illustrates an exemplary block diagram of a disease detection platform, according to an exemplary embodiment of the present disclosure.

FIG. 1B illustrates an exemplary block diagram of a disease detection platform 100 for determining specimen property or image property information pertaining to digital pathology image(s), using machine learning. The disease detection platform 100 may include a slide analysis tool 101, a data ingestion tool 102, a slide intake tool 103, a slide scanner 104, a slide manager 105, a storage 106, a laboratory information system 107 and a viewing application tool 108.

The slide analysis tool 101, as described below, refers to a process and system for determining data variable property or health variable property information pertaining to digital pathology image(s). Machine learning may be used to classify an image, according to an exemplary embodiment. The slide analysis tool 101 may also predict future relationships, as described in the embodiments below.

The data ingestion tool 102 may facilitate a transfer of the digital pathology images to the various tools, modules, components, and devices that are used for classifying and processing the digital pathology images, according to an exemplary embodiment.

The slide intake tool 103 may scan pathology images and convert them into a digital form, according to an exemplary embodiment. The slides may be scanned with slide scanner 104, and the slide manager 105 may process the images on the slides into digitized pathology images and store the digitized images in storage 106.

The viewing application tool 108 may provide a user with a specimen property or image property information pertaining to digital pathology image(s), according to an exemplary embodiment. The information may be provided through various output interfaces (e.g., a screen, a monitor, a storage device and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over a network 120. Further, server systems 110 may include storage devices for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively, or in addition, the present disclosure (or portions of the system and methods of the present disclosure) may be performed on a local processing device (e.g., a laptop).

Any of the above devices, tools and modules may be located on a device that may be connected to an electronic network such as the Internet or a cloud service provider, through one or more computers, servers and/or handheld mobile devices.

Figure 1C:
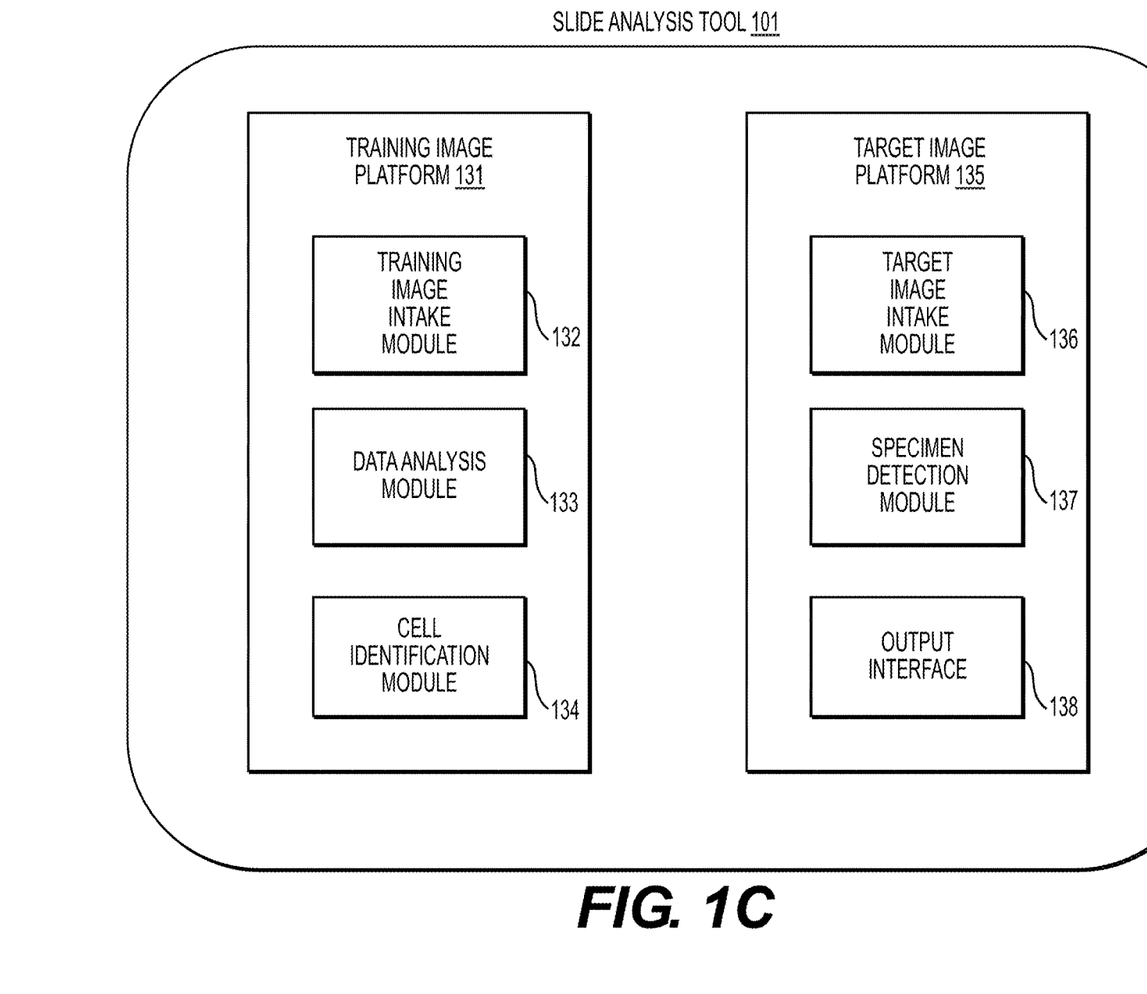
FIG. 1C illustrates an exemplary block diagram of a slide analysis tool, according to an exemplary embodiment of the present disclosure.

FIG. 1C illustrates an exemplary block diagram of a slide analysis tool 101, according to an exemplary embodiment of the present disclosure. The slide analysis tool 101 may include a training image platform 131 and/or a target image platform 135.

According to one embodiment, the training image platform 131 may include a training image intake module 132, a data analysis module 133, and a cell identification module 134.

The training image platform 131, according to one embodiment, may create or receive training images that are used to train a machine learning model to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized tissue samples from a 3D imaging device, such as microCT.

The training image intake module 132 may create or receive a dataset comprising one or more training datasets corresponding to one or more health variables and/or one or more data variables. For example, the training datasets may be received from any one or any combination of the server systems 110, physician servers 121, hospital servers 122, clinical trial servers 123, research lab servers 124, and/or laboratory information systems 125. This dataset may be kept on a digital storage device. The data analysis module 133 may identify whether a set of individual cells belong to a cell of interest or a background of a digitized image. The cell identification module 134 may analyze digitized images and determine whether an individual cell in the cytology sample needs further analysis. It is useful to identify whether an individual cell needs further analysis and to aggregate these areas, and the identification of such may trigger an alert to a user.

According to one embodiment, the target image platform 135 may include a target image intake module 136, a specimen detection module 137, and an output interface 138. The target image platform 135 may receive a target image and apply the machine learning model to the received target image to determine a characteristic of a target data set. For example, the target data may be received from any one or any combination of the server systems 110, physician servers 121, hospital servers 122, clinical trial servers 123, research lab servers 124, and/or laboratory information systems 125. The target image intake module 136 may receive a target dataset corresponding to a target health variable or a data variable. Specimen detection module 137 may apply the machine learning model to the target dataset to determine a characteristic of the target health variable or a data variable. For example, the specimen detection module 137 may detect a trend of the target relationship. The specimen detection module 137 may also apply the machine learning model to the target dataset to determine a quality score for the target dataset. Further, the specimen detection module 137 may apply the machine learning model to the target images to determine whether a target element is present in a determined relationship.

The output interface 138 may be used to output information about the target data and the determined relationship. (e.g., to a screen, monitor, storage device, web browser, etc.).

Figure 2:
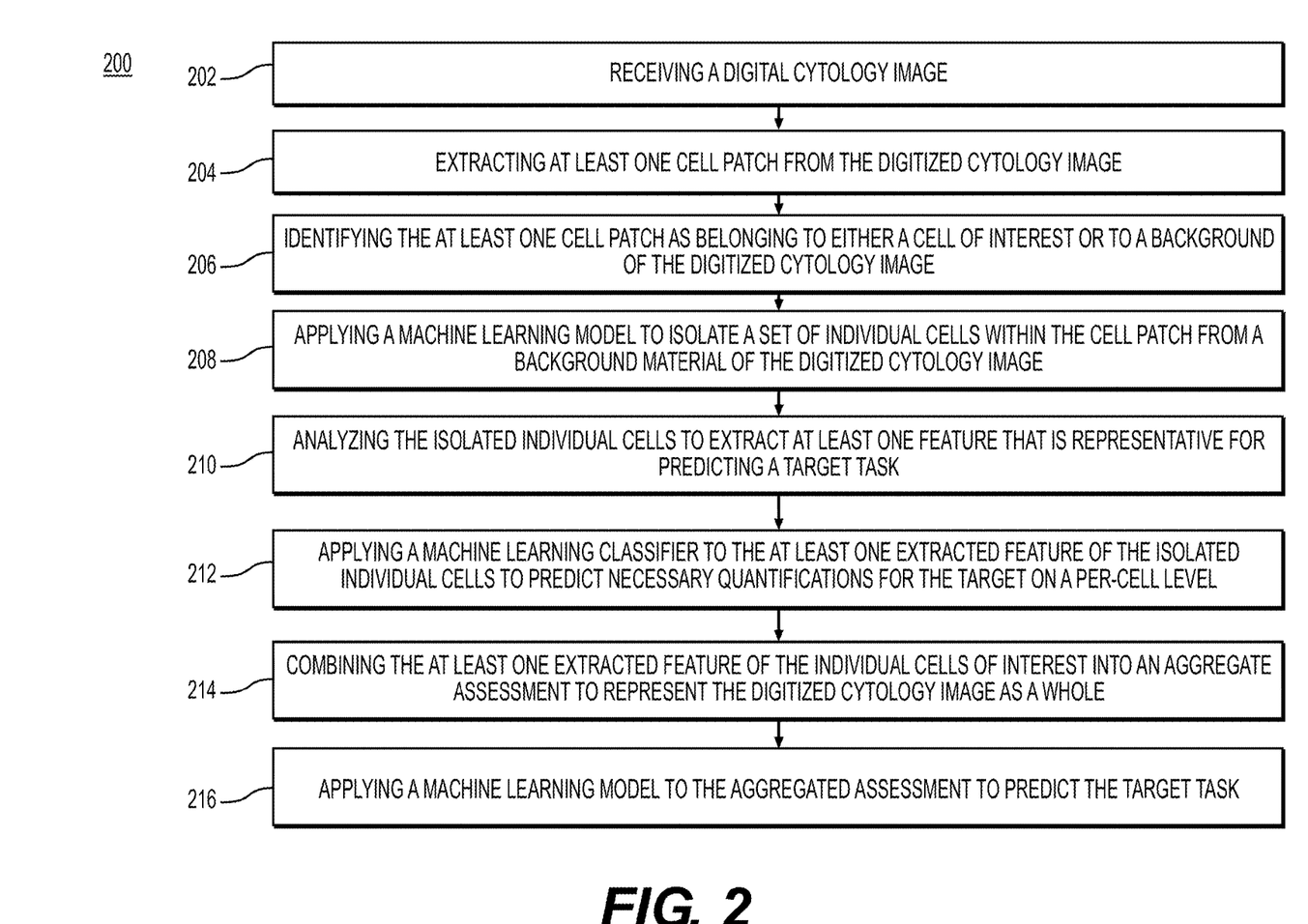
FIG. 2 is a flowchart illustrating an exemplary method for predicting a target task from a cytology specimen, according to an exemplary embodiment of the present disclosure.

FIG. 2 is a flowchart illustrating an exemplary method for predicting a target task from a cytology specimen, according to an exemplary embodiment of the present disclosure. For example, a target task 200 may be to assess adequacy of the specimen using cellularity by identifying individual cells (e.g., steps 202-210), then counting the number of non-malignant cells using a machine learning method 212, which may be performed by slide analysis tool 101 automatically or in response to a request from a user.

According to an exemplary embodiment 200, the artificial intelligence (AI) detection system may be comprised of three components: cell isolation, cell feature extraction, and output aggregation. Cell isolation extracts individual cell patches from the cytology image, feature extraction identifies important morphological features from the cell, and output aggregation combines all the cellular features into a final output prediction depending on the task. The input to the system may be a digital cytology image, and the output may be a task-specific prediction including but not limited to diagnosis, prognosis, or treatment decision. These three components may include one or more of the following steps.

In step 202, the method may include receiving a digital cytology image into a digital storage device.

In step 204, the method may include extracting at least one cell patch from the digitized cytology image.

In step 206, the method may include identifying the at least one cell patch as belonging to either a cell of interest or to a background of the digitized cytology image.

In step 208, the method may include applying a machine learning model to isolate a set of individual cells within the cell patch from the background material of the digitized cytology image. The process of cell isolation identifies individual cells within the cytology image, separating the cells of interest from the background material within the fluid. Isolating each cell may be accomplished by a machine learning model trained to identify the cell type of interest. The machine learning model can take the form of a detection or segmentation system. The detection approach identifies bounding regions for each cell and can be accomplished by a variety of methods including but not limited to:
  a) Sliding-window approaches using region features such as Haar wavelets or histogram of oriented gradients (HOG) and a classifier such as boosting, support vector machine (SVM), or deformable parts models (DPM).
  b) Region proposal-based methods using deep learning such as region-based convolutional neural networks (R-CNN), spatial pyramid pooling (SPP-net), you only look once (YOLO) and single shot detector (SSD).

Segmentation identifies individual pixels as belonging to the cell of interest or background. Segmentation can also classify cell regions into more granular structures such as identifying the nucleus, cytoplasm, and other sub-cellular features. Methods for segmentation can include but is not limited to:
  a) Edge-based segmentation, histogram-based segmentation, region growing, graph partitioning and watershed methods.
  b) Deep learning methods such as UNet, DeepLab and other fully convolutional network (FCN) variants.

Detection and segmentation can also be combined into a panoptic instance segmentation system using, but not limited to, the following methods:
 a) Mask R-CNN
 b) Deep Mask
 c) PolyTransform
 d) Detection Transformers (DETR)

The output of the cell isolation system may be a set of sub-images tightly bounded around each cell of interest within the cytology image.

In step 208, the method may include applying a machine learning model to isolate a set of individual cells within the cell patch from a background material of the digitized cytology image.

In step 210, the method may include analyzing the isolated individual cells to extract at least one feature that is representative for predicting a target task.

Each isolated cell may be analyzed by the machine learning model to extract features that are representative for predicting the target task. Methods for extracting these features can include, but are not limited to:
 1. Color descriptors, shape features, texture descriptors
 2. Features trained from deep learning models In step 212, the method may include applying a machine learning classifier to the at least one extracted feature of the isolated individual cells to predict necessary quantifications for the target task on a per-cell level.

These features may be used to train a machine learning classifier to predict necessary quantifications for the target task on a per-cell level. These quantifications may include identifying the presence of cancer, genetic mutation, hypertrophy, etc.

In step 214, the method may include combining the at least one extracted feature of the individual cells of interest into an aggregate assessment to represent the digitized cytology image as a whole. This aggregation can be achieved by a variety of approaches, including computing statistics of the per-cell classifications, estimating feature means or cluster centers, and training deep learning aggregators that combine per-cell features through convolutional or recurrent mechanisms.

Once each cell is classified, the results for all cells in the cytology image are combined into an aggregate assessment to achieve a final prediction of the target task.

In step 216, the method may include applying a machine learning model to the aggregate assessment to predict the target task. The final aggregated feature may also be used to train a final machine learning model to predict the target task. This can include methods such as SVM, logistic regression, and regression or classification-based neural networks.

Using a Machine Learning Model to Predict the Target Task

According to an exemplary embodiment, one or more steps for performing a method may include the following steps. All steps are optional and may be used in any order.
 1. Receive digitized liquid sample.
 2. Optionally receive meta data (e.g. patient clinical information)
 3. An AI-based system may be used to generate a result
 4. The prediction may be outputted to an electronic storage device and/or display.
 5. The user (e.g. Pathologist, oncologist, patient, etc.) may be made aware that results are available, for example via push or pull notification, user interface popup, a noise, etc.
 6. Optionally, the user may be provided the option to review visualization and/or report. This may also occur automatically.

The present disclosure may be implemented in the following ways for the user, including but not limited to:
 1. Within the clinical workflow at the hospital, lab, medical center as a:
  a. Web application (cloud-based or on-premises)
  b. Mobile application
  c. Interactive report
  d. Static report
  e. Dashboard
 2. Multiple features can be visualized for a single whole slide image.

The technical workflow behind an embodiment of the present disclosure may be as follows:
 1. Digitized whole slide image may be created and some or all metadata may be made available from hospital and/or hardware databases
 2. Image and corresponding data may be passed into the appropriate AI-based system and outputs are generated
 3. Some of the outputs may be fed into the system that will generate and display the visualization to the user. Visualization to the user can be in the form of a:
  a. Report
  b. Overlay in a web application, and/or
  c. Exportable file.

The method above may have many possible specific applications or embodiments, as described below. All steps are optional and may be used in any order.

Evaluation of Adequacy of Non-Malignant Cells

Various classification/categorization systems have definitions of adequacy to ensure that each sample contains enough material for the user to definitively categorize the sample. An exemplary embodiment of the present disclosure for this application may be as follows.

Figure 3:
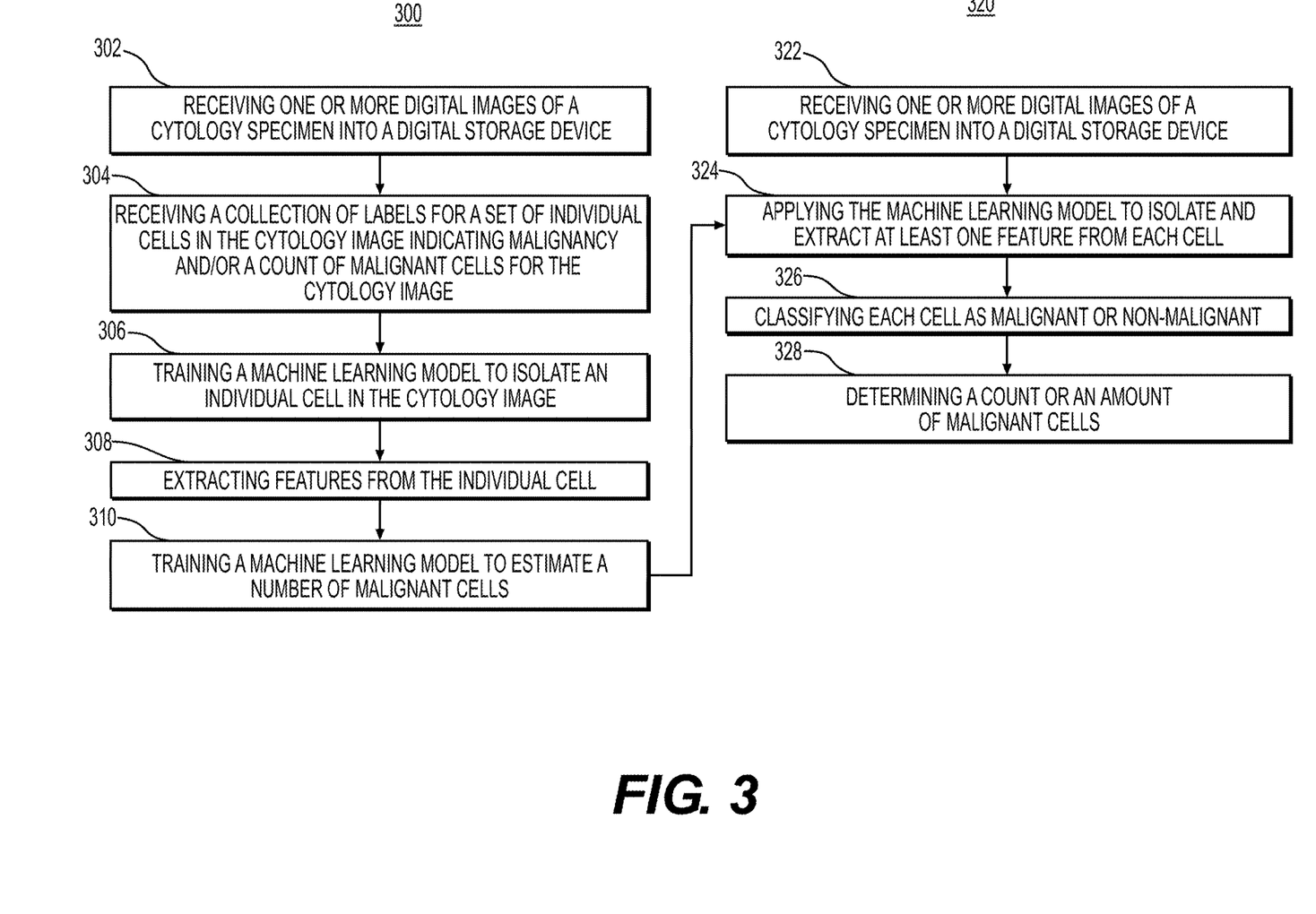
FIG. 3 is a flowchart illustrating an exemplary method for evaluating an adequacy of non-malignant cells in a pathology specimen, according to an exemplary embodiment of the present disclosure

FIG. 3 is a flowchart of an exemplary method for evaluating the adequacy of non-malignant cells, according to an exemplary embodiment of the present disclosure. For example, exemplary methods 300 and 320 (e.g., steps 302-310 and steps 322-328) may be performed by the slide analysis tool 101 automatically or in response to a request by a user (e.g., a physician).

In step 302, the method may include receiving one or more digital images of a cytology specimen into a digital storage device (e.g. hard drive, network drive, cloud storage, system memory, etc.).

In step 304, the method may include receiving a collection of labels for a set of individual cells in the cytology image indicating malignancy and/or a count of malignant cells for the cytology image.

In step 306, the method may include training a machine learning model to isolate an individual cell in the cytology image, as described above and in FIG. 2.

In step 308, the method may include extracting features from the set of individual cells, as described above and in FIG. 2.

In step 310, the method may include training a machine learning model to estimate a number of malignant cells. If ground-truth labels are provided to determine if each cell is malignant or non-malignant, a model can be trained in a fully-supervised manner using the cell features as input. The model can consist of an SVM, random forest, CNN, etc.

If only a malignant cell count is available, an aggregation network can be trained to regress the malignant cell count from the collection of cell features. This can utilize neural network models such as a recurrent neural network (RNN) or convolutional neural network (CNN).

In step 322, the method may include receiving one or more digital images of a cytology specimen into a digital storage device (e.g. hard drive, network drive, cloud storage, system memory, etc.).

In step 324, the method may include applying the machine learning model to isolate and extract at least one feature from each cell.

In step 326, the method may include classifying each cell as malignant or non-malignant.

In step 328, the method may include determining a count or amount of malignant cells. If a fully-supervised model was trained to classify malignant cells, malignant cells can be counted to determine adequacy. Otherwise, the regression model can be used to directly estimate the count.

Categorization of Specimen

Various classification/categorization systems may be used for certain cytologic samples (e.g. Bethesda for cervical/Pap and thyroid samples, Paris for urine samples, Milan for salivary samples). Based on the morphological features present on the slide, the present disclosure identifies the specimen type and selects the appropriate categorization system for classifying the findings in the specimen.

For Training:
1. One or more digital images of a cytology specimen may be received at a digital storage device or processor (e.g. hard drive, network drive, cloud storage, system memory, etc.).
2. A label for each cytology image may be received indicating the categorization system, and the category of the specimen.
3. A machine learning algorithm may be trained to classify the specimen type. This may be learned directly from the cytology image using algorithms such as CNN, random forest, or SVM. This may also be learned by cell isolation and feature aggregation as described in the general form of the present disclosure. Determination of the specimen type may also determine the categorization system.
4. The cells may be isolated and cellular features may be extracted as described in the general form of the present disclosure.
5. The output aggregation model may be trained to combine cells features to predict the category using the target labels specified in step 2.

For Use:
1. One or more digital images of a cytology specimen may be received a digital storage device and/or display (e.g. hard drive, network drive, cloud storage, system memory, etc.).
2. The specimen type may be classified using the trained specimen classification model.
3. The cells and may be isolated and cellular features may be extracted as described in the general form of the present disclosure.
4. The specimen category may be classified from the cellular features using the trained output aggregation model.

Screening for Mutations

Specific cancers can exhibit mutations detected by fluorescence in situ hybridization (FISH) or next-generation sequencing (NGS). These mutations may be prognostic or have therapeutic implications. The present disclosure may allow an algorithm to predict the probability of detecting specific mutations in tumor cells within a cytologic preparation by FISH or NGS.

For Training:
1. One or more digital images of a cytology specimen may be received at a processor and/or digital storage device (e.g. hard drive, network drive, cloud storage, system memory, etc.).
2. Labels for individual cells may be received in the cytology image indicating if they are malignant or not.
3. Labels for individual cells in the cytology image may originate from spatial genomics to identify specific gene mutations or biomarkers for each cell that correlate with malignancy; e.g. EGFR, ALK, KRAS, ROS1, RET, etc. for lung, BRAF, NRAS, RET, etc. for thyroid, IDH1, IDH2, FLT3, NPM1, 17p-, etc. for bone marrow aspirates, etc.
4. A machine learning algorithm may be trained to isolate each cell as described in the general form of the present disclosure.
5. Features may be extracted from each cell as described in the general form of the present disclosure.
6. A machine learning algorithm may be trained to classify if a cell is malignant or not using the cellular features extracted in the previous step and the target labels in step 2. The model may consist of an SVM, random forest, CNN, etc.
7. The above model may be used to isolate only the cells that are malignant and train a machine learning algorithm to classify the presence of the mutation in that cell using the target mutation labels in step 3. The model can consist of an SVM, random forest, CNN, etc.

For Use:
1. One or more digital images may be received of a cytology specimen into a digital storage device (e.g. hard drive, network drive, cloud storage, system memory, etc.).
2. The machine learning algorithm may be applied to isolate and extract features from each cell.
3. Each cell may be classified as malignant or non-malignant.
4. The malignant cells may be isolated. The presence of any mutation and a corresponding classification score may be predicted.

Figure 4:
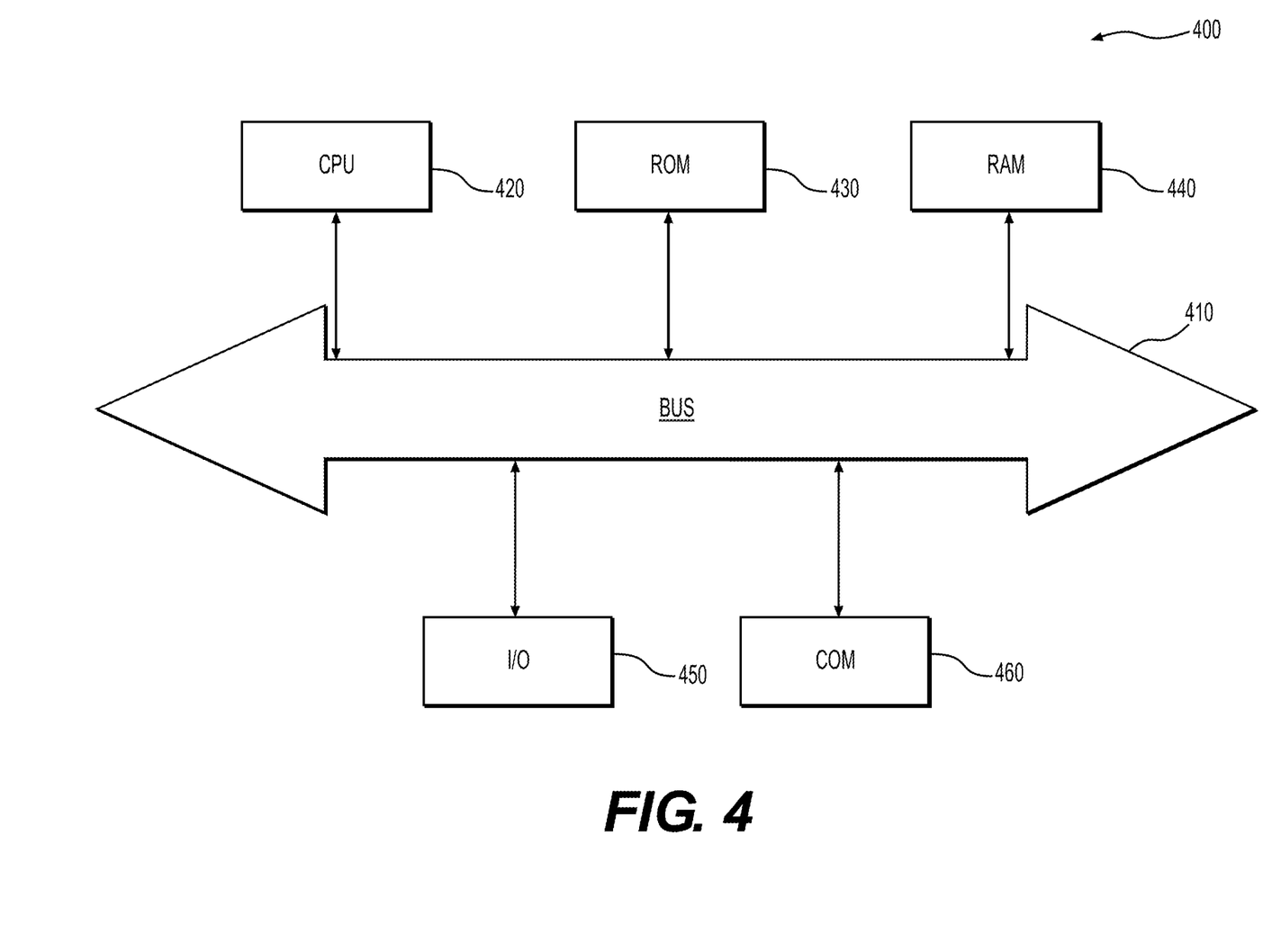
FIG. 4 illustrates an example system that may execute techniques presented herein.

As shown in FIG. 4, device 400 may include a central processing unit (CPU) 420. CPU 420 may be any type of processor device including, for example, any type of special purpose or a general-purpose microprocessor device. As will be appreciated by persons skilled in the relevant art, CPU 420 also may be a single processor in a multi-core/multi-processor system, such system operating alone, or in a cluster of computing devices operating in a cluster or server farm. CPU 420 may be connected to a data communication infrastructure 410, for example a bus, message queue, network, or multi-core message-passing scheme.

Device 400 may also include a main memory 440, for example, random access memory (RAM), and also may include a secondary memory 430. Secondary memory 430, e.g. a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 430 may include similar means for allowing computer programs or other instructions to be loaded into device 400. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 400.

Device 400 also may include a communications interface ("COM") 460. Communications interface 460 allows software and data to be transferred between device 400 and external devices. Communications interface 460 may include a modem, a network interface (such as an Ethernet card), a communications port, a PCMCIA slot and card, or the like. Software and data transferred via communications interface 460 may be in the form of signals, which may be electronic, electromagnetic, optical or other signals capable of being received by communications interface 460. These signals may be provided to communications interface 460 via a communications path of device 400, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 400 may also include input and output ports 450 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically can be grouped together to perform a function or group of related functions. Like reference numerals are generally intended to refer to the same or similar components. Components and modules may be implemented in software, hardware or a combination of software and hardware.

The tools, modules, and functions described above may be performed by one or more processors. "Storage" type media may include any or all of the tangible memory of the computers, processors, or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments of the invention will be apparent to those skilled in the art from consideration of the specification and practice of the invention disclosed herein. It is intended that the specification and examples to be considered as exemplary only.

What is claimed is:

1. A computer-implemented method for identifying a specimen category, comprising:
   receiving one or more digital images of a cytology specimen at a digital storage device;
   extracting at least one cell patch from the one or more digital images;
   identifying the at least one cell patch as belonging to either cell or background;
   isolating one or more cell images using the digital images, wherein isolating the one or more cell images comprises isolating a set of individual images of cells within the cell patch using a segmentation system and/or a detection system;
   extracting one or more cellular features using the cell images; and
   determining a specimen category from the one or more cellular features using a trained output aggregation model.

2. The computer-implemented method of claim 1, further comprising training the trained output aggregation model by:
   receiving one or more training digital images of at least one cytology specimen;
   receiving at least one training label for the cytology specimen indicating a categorization system and a category of the cytology specimen;
   isolating one or more cell images using the one or more training digital images; and
   extracting one or more cellular features from the one or more isolated cell images.

3. The computer-implemented method of claim 2, wherein training the trained output aggregation model includes training the trained output aggregation model to combine the one or more extracted cellular features using the at least one training label.

4. The computer-implemented method of claim 2, wherein outputting the specimen category includes outputting a visualization and/or a report of the specimen category.

5. The computer-implemented method of claim 1, further comprising training at least one of the trained output aggregation model or a trained specimen classification model to classify a specimen type for a cytology specimen.

6. The computer-implemented method of claim 5, further comprising determining a specimen type from the received one or more digital images using the trained output aggregation model or the trained specimen classification model.

7. The computer-implemented method of claim 1, further comprising:
   selecting an appropriate categorization system for the one or more cellular features in the cytology specimen.

8. The computer-implemented method of claim 1, further comprising combining the one or more cellular features in the cytology specimen into an aggregate assessment to represent the digital cytology image as a whole.

9. The computer-implemented method of claim 1, further comprising:
   notifying a user that the specimen category is available; and
   providing the user an option to review a visualization and/or a report of the specimen category.

10. The computer-implemented method of claim 1, further comprising:
    outputting the specimen category to a digital storage device and/or display.

11. A system for identifying a specimen category, comprising:
- at least one memory storing instructions; and
- at least one processor configured to execute the instructions to perform operations comprising:

receiving one or more digital images of a cytology specimen at a digital storage device;
- extracting at least one cell patch from the one or more digital images;
- identifying the at least one cell patch as belonging to either cell or background;
- isolating one or more cell images using the digital images, wherein isolating the one or more cell images comprises isolating a set of individual images of cells within the cell patch using a segmentation system and/or a detection system;
- extracting one or more cellular features using the cell images; and
- determining a specimen category from the one or more cellular features using a trained output aggregation model.

12. The system of claim 11, wherein the operations further comprise training the trained output aggregation model by:
- receiving one or more training digital images of at least one cytology specimen;
- receiving at least one training label for the cytology specimen indicating a categorization system and a category of the cytology specimen;
- isolating one or more cell images using the one or more training digital images; and
- extracting one or more cellular features from the one or more isolated cell images.

13. The system of claim 12, wherein training the trained output aggregation model includes training the trained output aggregation model to combine the one or more extracted cellular features using the at least one training label.

14. The system of claim 11, further comprising at least one of a display or a digital storage device, wherein the operations further comprise outputting the specimen category to the at least one of the display or the digital storage device.

15. A non-transitory computer readable medium storing instructions that, when executed by a processor, cause the processor to perform a method for identifying a specimen category, the method comprising:
- receiving one or more digital images of a cytology specimen at a digital storage device;
- extracting at least one cell patch from the one or more digital images;
- identifying the at least one cell patch as belonging to either cell or background;
- isolating one or more cell images using the digital images, wherein isolating the one or more cell images comprises isolating a set of individual images of cells within the cell patch using a segmentation system and/or a detection system;
- extracting one or more cellular features using the cell images; and
- determining a specimen category from the one or more cellular features using a trained output aggregation model.

* * * * *